United States Patent [19]

Clough et al.

[11] Patent Number: 4,684,396
[45] Date of Patent: Aug. 4, 1987

[54] TRIAZOLE AND IMIDAZOLE COMPOUNDS USEFUL AS PLANT GROWTH REGULATORS AND FUNGICIDES

[75] Inventors: John M. Clough, High Wycombe; David A. Griffin, Berkshire, both of England

[73] Assignee: Imperial Chemical Industries Plc, London, England

[21] Appl. No.: 696,169

[22] Filed: Jan. 29, 1985

[30] Foreign Application Priority Data

Mar. 1, 1984 [GB] United Kingdom ............... 8405368

[51] Int. Cl.$^4$ ............... A01N 43/653; C07D 249/08
[52] U.S. Cl. ............................. 07/92; 514/184; 514/383; 514/399; 548/101; 548/262; 548/341
[58] Field of Search .................. 548/101, 262, 341; 514/184, 383, 399; 71/92

[56] References Cited

U.S. PATENT DOCUMENTS 4,118,461 10/1978 Miller et al. ............... 548/101 X
4,518,415 5/1985 Marchington et al. ......... 548/262 X

FOREIGN PATENT DOCUMENTS 0060223 3/1982 European Pat. Off.
2735872 2/1978 Fed. Rep. of Germany.
0064245 11/1982 Fed. Rep. of Germany.
2110684 6/1983 United Kingdom.

OTHER PUBLICATIONS

Chemical Abstracts, vol. 99, No. 3, Jul. 18, 1983, Columbus, Ohio, USA, Eshima et al., "Cyclodextrin-Capped Iron-Prophyrin Derivatives, I. Heme Complex with the Imidazole Derivatives Included in Cyclodextrin", p. 592, col. 1, Abstract No. 22-196q and Nippon Kagaku Kaishi, 1983, (2), 214-218.
Chemical Abstracts, vol. 89, No. 3, Jul. 17, 1978, Columbus, Ohio, USA, Miller, A. D., "Triazole Derivatives", p. 658, col. 1, Abstract No. 24 368q and S. African 76 06,188.
Chemical Abstracts, vol 91, No. 19, Nov. 5, 1979, Columbus, Ohio, USA, Wellcome Foundation Ltd. "1-Substituted Imidazoles and Medicinal Compositions Containing Them", p. 642, col. 1, Abstract No. 157 734u and Jpn. Kokai Tokkyo Koho 79 55,568.
Chemical Abstracts, vol. 91, No. 17, Oct. 22, 1979, Columbus, Ohio, USA, Wellcome Foundation Ltd. "1-Alkylimidazoles", p. 660, Col. 1, Abstract No. 140 844g and Jpn. Kokai Tokkyo Koho 79 52,078.

Primary Examiner—Richard L. Raymond
Attorney, Agent, or Firm—Cushman, Darby & Cushman

[57] ABSTRACT

A compound having the general formula (I):

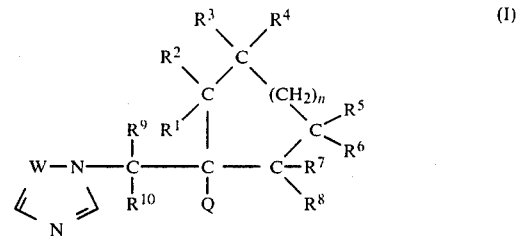

and stereoisomers thereof, wherein W is CH or N; Q is optionally substituted aryl, optionally substituted aralkyl, or alkyl; $R^1$, $R^2$, $R^3$, $R^4$, $R^5$, $R^6$, $R^7$, and $R^8$, which may be the same or different, are H, hydroxy, alkyl, cycloalkyl, optionally substituted aralkyl, or optionally substituted phenyl, or any of the pairs $R^1$ and $R^2$; $R^3$ and $R^4$; $R^5$ and $R^6$; or $R^7$ and $R^8$ can, together with the adjacent ring carbon atom, represent a carbonyl group (C=O); $R^9$ and $R^{10}$ which may be the same or different, are H, alkyl, cycloalkyl, optionally substituted aralkyl, or optionally substituted phenyl; n is 0 or 1; and acid salts and metal complexes thereof. The compounds have plant growth regulating and fungicidal activity.

12 Claims, No Drawings

TRIAZOLE AND IMIDAZOLE COMPOUNDS USEFUL AS PLANT GROWTH REGULATORS AND FUNGICIDES

This invention relates to triazole and imidazole compounds useful as plant growth regulators and fungicides, to processes for preparing them, to plant growth regulatory and fungicidal compositions containing them, and to methods of using them to regulate plant growth and to combat fungi, especially fungal infections in plants.

The invention provides a compound having the general formula (I):

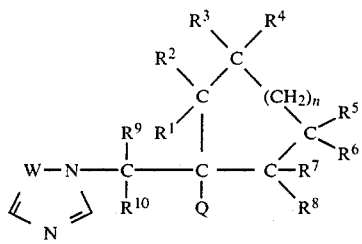

and stereoisomers thereof, wherein W is CH or N; Q is optionally substituted aryl (especially optionally substituted phenyl), optionally substituted aralkyl, or alkyl; $R^1$, $R^2$, $R^3$, $R^4$, $R^5$, $R^6$, $R^7$, and $R^8$, which may be the same or different, are H, hydroxy, alkyl, cycloalkyl, optionally substituted aralkyl, or optionally substituted phenyl, or any of the pairs $R^1$ and $R^2$; $R^3$ and $R^4$; $R^5$ and $R^6$; or $R^7$ and $R^8$ can, together with the adjacent ring carbon atom, represent a carbonyl group (C=O); $R^9$ and $R^{10}$ which may be the same or different, are H, alkyl, cycloalkyl; optionally substituted aralkyl, or optionally substituted phenyl; n is 0 or 1; and acid salts and metal complexes thereof.

Preferred alkyl groups contain from 1 to 6, especially 1 to 4, carbon atoms. Preferred cycloalkyl groups are cyclopropyl, cyclobutyl, cyclopentyl, and cyclohexyl. The alkyl moiety in aralkyl groups preferably contains from 1 to 4 carbon atoms.

The compounds of the invention may contain chiral centres. Such compounds are generally obtained in the form of racemic mixtures. However, these and other mixtures can be separated into the individual isomers by methods known in the art, and this invention embraces such isomers.

Examples of suitable substituent groups for Q, $R^1$, $R^2$, $R^3$, $R^4$, $R^5$, $R^6$, $R^7$, $R^8$, $R^9$ and $R^{10}$ when they represent aralkyl or aryl, especially benzyl or phenyl, are halogen, haloalkyl, alkyl, alkoxy (especially containing 1 to 4 carbon atoms), optionally substituted phenyl and optionally substituted phenoxy. Phenyl is preferred to benzyl.

Suitably the aryl, especially phenyl group is unsubstituted or substituted with 1, 2 or 3 ring substituents, which may be the same or different, as defined above. Examples of Q, $R^1$, $R^2$, $R^3$, $R^4$, $R^5$, $R^6$, $R^7$, $R^8$, $R^9$ and $R^{10}$ are phenyl, 2-, 3- or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3- or 4-ethoxyphenyl, 2-fluoro-4-chlorophenyl, 2-chloro-4-fluorophenyl, 2-, 3- or 4-methyl-phenyl, 2-, 3- or 4-ethylphenyl, 2-, 3- or 4-trifluoro-methylphenyl, 4-phenylphenyl (4-biphenylyl), 2-chloro-4-methoxyphenyl, 2-fluoro-4-methoxyphenyl, 2-chloro-4-methylphenyl, 2-fluoro-4-methylphenyl, 4-isopropylphenyl, 2-methyl-4-chlorophenyl or 2-methyl-4-fluorophenyl.

When Q, $R^1$, $R^2$, $R^3$, $R^4$, $R^5$, $R^6$, $R^7$, $R^8$, $R^9$ or $R^{10}$ is alkyl it can be a straight or branched chain alkyl group having 1 to 6, eg. 1 to 4 carbon atoms; examples are methyl, ethyl, propyl (n- or iso-propyl) and butyl (n-, sec-, iso- or t-butyl). Q is preferably t-butyl.

The moiety W is preferably N, ie. the preferred compounds are triazoles.

The salts can be salts with inorganic or organic acids eg. hydrochloric, nitric, sulphuric, acetic, 4-toluenesulphonic or oxalic acid.

Suitably the metal complex is one including, as the metal, copper, zinc, manganese or iron. It preferably has the formula:

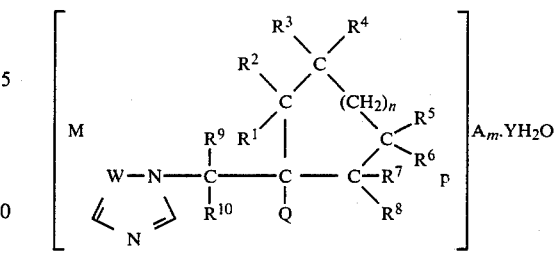

wherein W, Q, $R^1$, $R^2$, $R^3$, $R^4$, $R^5$, $R^6$, $R^7$, $R^8$, $R^9$, $R^{10}$ and n are as defined above, M is a metal, A is an anion (eg. a chloride, bromide, iodide, nitrate, sulphate or phosphate anion), p is 2 or 4, y is 0 or an integer of 1 to 12, and m is an integer consistent with valency.

Examples of the compounds of the invention are shown in Table I. These conform to formula I and in each instance the groups $R^5$, $R^6$, $R^7$, $R^8$, $R^9$ and $R^{10}$ are hydrogen.

TABLE I

| COMPOUND NO | Q | $R^1$ | $R^2$ | $R^3$ | $R^4$ | W | n | Melting Point (°C.) |
|---|---|---|---|---|---|---|---|---|
| 1 | $C_6H_5$ | | | H | H | N | 0 | 106.5–107.5 |
| 2 | 2,4-di-Cl—$C_6H_3$ | | | $CH_3$ | H | N | 0 | Oil* |
| 3 | 4-Cl—$C_6H_4$ | | | $CH_3$ | H | N | 0 | Oil+ |
| 4 | 2,4-di-Cl—$C_6H_3$ | | | n-$C_3H_7$ | H | N | 0 | Oil+ |
| 5 | 4-Cl—$C_6H_4$ | | | $CH_3$ | $CH_3$ | N | 0 | 88–90 |
| 6 | 4-Cl—$C_6H_4$ | | | H | H | N | 1 | Oil |
| 7 | 4-Cl—$C_6H_4$ | OH | H | H | H | N | 1 | Oil |
| 8 | 4-Cl—$C_6H_4$ | OH | $CH_3$ | H | H | N | 1 | 172.5–175.0 |

*1:2 mixture of diastereomers
+1:3 mixture of diastereomers

The compounds of the invention having the general formula (I):

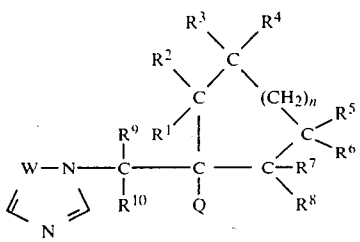

(I)

wherein Q, W, $R^1$, $R^2$, $R^3$, $R^4$, $R^5$, $R^6$, $R^7$, $R^8$, $R^9$ and $R^{10}$ and n are as defined above, can be prepared by treatment of cycloalkanes of general formula (II):

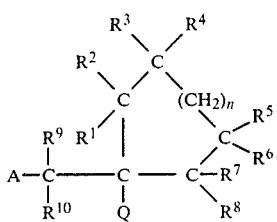

(II)

wherein Q, $R^1$, $R^2$, $R^3$, $R^4$, $R^5$, $R^6$, $R^7$, $R^8$, $R^9$ and $R^{10}$ and n are as defined above and A is a leaving group, for example a halogen (preferably bromine, chlorine or iodine) or a sulphonate group (for example, a $CH_3SO_2O-$ or $4-CH_3-C_6H_4-SO_2O-$ group), either with 1,2,4-triazole or with imidazole, each in the presence of an acid-binding agent or on the form of one of its alkali metal salts, in a convenient solvent (such as dimethylformamide or acetonitrile) and at a convenient temperature (such as 60° to 160° C.).

Cycloalkanes of general formula (II) can be prepared from alcohols of general formula (III):

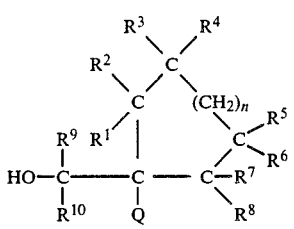

(III)

wherein Q, $R^1$, $R^2$, $R^3$, $R^4$, $R^5$, $R^6$, $R^7$, $R^8$, $R^9$ and $R^{10}$ and n are as defined above, either (a) by a standard halogenation procedure (A is a halogen) or (b) by a standard esterification procedure (using, for example, mesyl chloride or tosyl chloride, each in the presence of a base: A is a $CH_3SO_2O-$ or a $4-CH_3-C_6H_4-SO_2O-$ group).

Alcohols of general formula (III) can be prepared from carboxylic esters of general formula (IV):

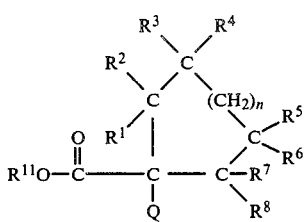

(IV)

wherein Q, $R^1$, $R^2$, $R^3$, $R^4$, $R^5$, $R^6$, $R^7$ and $R^8$ and n are as defined above and $R^{11}$ is an alkyl, cycloalkyl or aralkyl group (preferably a simple alkyl group such as a methyl or ethyl group), either (a) by reduction using, for example, lithium aluminium hydride ($R^9=R^{10}=H$) or (b) by treatment with a Grignard reagent of general formula (V):

$$R^9-Mg-X \qquad (V)$$

wherein $R^9$ is as defined above and X is a halogen ($R^9=R^{10}$).

Grignard reagents of general formula (V) can be prepared from the corresponding halides, $R^9X$, by standard methods described in the chemical literature.

Compounds of general formula (III) in which $R^{10}$ is hydrogen and $R^9$ is not hydrogen can be prepared either (a) by partial reduction of esters of general formula (IV) to the corresponding aldehydes followed by treatment with Grignard reagents of general formula (V) or (b) by partial oxidation of alcohols of general formula (III) in which $R^9=R^{10}=H$ to the corresponding aldehydes, followed by treatment with Grignard reagents of general formula (V).

Esters of general formula (IV) can be prepared from acids of general formula (VI):

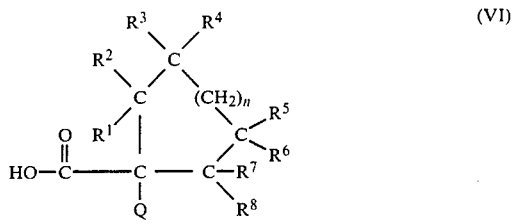

(VI)

wherein Q, $R^1$, $R^2$, $R^3$, $R^4$, $R^5$, $R^6$, $R^7$ and $R^8$ and n are as defined above, by one of the standard esterification procedures.

Acids of general formula (VI) can be prepared by acid- or base-catalysed hydrolysis of the corresponding nitriles of general formula (VII):

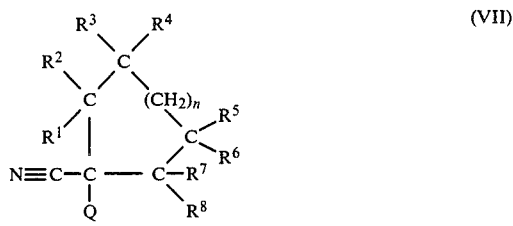

(VII)

wherein Q, $R^1$, $R^2$, $R^3$, $R^4$, $R^5$, $R^6$, $R^7$ and $R^8$ are as defined above. Alternatively, esters of general formula (IV) can be prepared directly by treatment of nitriles of general formula (VII) with alcohols of general formula $R^{11}OH$ under acidic conditions.

Nitriles of general formula (VII) can be prepared by bis-alkylation of nitriles of general formula (VIII):

$$Q-CH_2-C\equiv N \qquad (VIII)$$

wherein Q is as defined above, with compounds of general formula (IX):

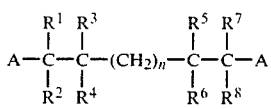
(IX)

wherein A, $R^1$, $R^2$, $R^3$, $R^4$, $R^5$, $R^6$, $R^7$ $R^8$ and n are as defined above, in the presence of an appropriate base. (For examples of related bis-alkylations see A Brandstrom and U Junggren, *Tetrahedron Lett.*, 1972, 473; K Tomioka and K Koga, *Tetrahedron Lett.*, 1980, 2321; D D Roberts, *J. Org. Chem.*, 1974, 39, 1265; R K Singh and S Danishefsky, *J. Org. Chem.*, 1975, 40, 2969; W Schneider and G Krombholz, *Arch. Pharm.*, 1980, 313, 487; P Brownbridge and S Warren, *J. C. S. Perkin I*, 1977, 2272).

Compounds of general formula (IX) can be prepared from the corresponding diols of general formula (X):

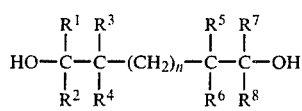
(X)

wherein $R^1$, $R^2$, $R^3$, $R^4$, $R^5$, $R^6$, $R^7$ and $R^8$ and n are as defined above, either (a) by bis-halogenation by one of the standard procedures described in the literature (A is halogen), or (b) by a standard double esterification procedure (using, for example, mesyl chloride or tosyl chloride, each in the presence of a base: A is a $CH_3SO_2O-$ or $4-CH_3-C_6H_4-SO_2-$ group. See, for example, T M Laakso and D D Reynolds, *J. Amer. Chem. Soc.*, 1951, 73, 3518).

Diols of general formula (X) can be prepared by standard methods as described in the chemical literature.

In an alternative approach, esters of general formula (IV) can be prepared directly by bis-alkylation of esters of general formula (XI):

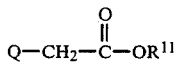
(XI)

wherein Q and $R^{11}$ are as defined above, with compounds of general formula (IX) in the presence of an appropriate base.

Compounds of formula III, where $R^1$ and $R^2$ together with the adjacent carbon atom represent carbonyl (ie. C=O) can be made by treating compounds of formula XII with an aldehyde of formula XIII in the presence of a base.

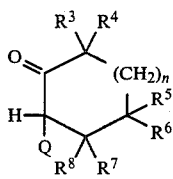
XII $R^9CHO$     XIII wherein $R^3$ to $R^9$, Q and n are as defined above.

Compounds of formula XII can be made by treating compounds of formula XIV with Grignard agents, QMgX; where X is a halogen.

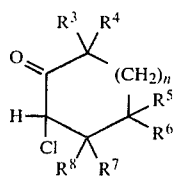
XIV

Compounds of formula I where $R^2$ is OH and $R^1$ is H can be made by reducing compounds of formula I, where $R^1$ and $R^2$ together with the adjacent carbon atom represent carbonyl, with standard reagents.

Compounds of formula I where $R^2$ is OH, and $R^1$ is not H, can be made by the action of a Grignard agent $R^1MgX$ (where X is a halogen) on compounds of formula I where $R^1$ and $R^2$ together with the adjacent carbon atom represent carbonyl.

The compounds, salts and metal complexes are active fungicides, particularly against the diseases:

*Piricularia oryzeae* on rice

*Puccinia recondita, Puccinia striiformis* and other rusts on wheat, *Puccinia hordei, Puccinia striiformis* and other rusts on barley, and rusts on other hosts eg. coffee, apples, apples, vegetables and ornamental plants

*Erysiphe graminis* (powdery mildew) on barley and wheat and other powdery mildews on various hosts such as *Sphaerotheca fuliginea* on cucurbits (eg. cucumber), *Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans

*Botrytis cinerea* (grey mould) on tomatoes, strawberries, vines and other hosts.

*Venturia inaequalis* (scab) on apples

Some of the compounds have also shown a broad range of activities against fungi in vitro. They have activity against various post-harvest diseases on fruit (eg. *Penicillium digatatum* and *italicum* on oranges and *Gloeosporium muscarum* on bananas). Further some of the compounds are active as seed dressings against: *Fusarium* spp., *Septoria* spp., *Tilletia* spp. (ie. bunt, a seed borne disease of wheat), *Ustilago* spp., *Helminthosporium* spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

The compounds are also useful for the treatment of candidiasis and human dermatophyte infections.

The compounds, and their derivatives as defined above, also have plant growth regulating activities, especially Compounds Nos 3, 4, 6 and 7 of Table I.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostic tenuis, Cynodon dactylon* (Bermuda grass), *Dactylis glomerata,* Festuca spp. (eg. *Festuca rubra*) and Poa spp. (eg. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (eg. Cyperus spp.) and dicotyledonous weeds (eg. daisy, plantain, knotweed, speedwell, thistle, docks and ragwort). The growth of non-crop vegetation (eg. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be used in this situation as they could restrict growth without killing the plants which would lead to soil erosion; at the same time the degree of competition for nutrients and water by the grass would be reduced and this would result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (eg. poinsettias, chrysanthemums, carnations, tulips and daffodils).

As indicated above, the compounds can also be used to stunt woody species. This property can be used to control hedgerows or to shape or reduce the need for pruning, of fruit trees (eg. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, eg. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (eg. rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, eg. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, eg. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (eg. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (ie. the harvested yield as a proportion of the total dry matter produced) by altering dry matter partitioning. This applies to all the aforements root, pod cereal, tree, plantation, and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides a fungicidal or plant growth regulating composition comprising a compound of general formula (I) as hereinbefore defined, or a salt, metal complex, ether or ester thereof; and, optionally, a carrier or diluent.

The invention also provides a method of combating fungi, which comprises applying to a plant, to seed of a plant, or to the locus of the plant or seed, a compound, or salt, metal complex, ether or ester thereof, as hereinbefore defined.

The invention also provides a method of regulating plant growth, which comprises applying to the plant, to seed of a plant or to the locus of a plant or seed, a compound, or salt, metal complex, ether or ester thereof, as hereinbefore defined.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compounds(s) having biological activity, eg. compounds having similar or complementary fungicidal or plant growth activity or compounds having plant growth regulating, herbicidal or insecticidal activity.

The other fungicidal compound can be, for example, one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimte, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are Pirimor, Croneton, dimethoate, Metasystox and formothion.

The other plant growth regulating compound can be one which controls weeds or seedhead formation, improves the level or longevity of the plant growth regulating activity of the compounds of general formula (I), selectively controls the growth of the less desirable plants (eg. grasses) or causes the compound of general formula (I) to act faster or slower as a plant growth regulating agent. Some of these other agents will be herbicides.

Examples of suitable plant growth regulating compounds, which can display synergy in admixture, or use, with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluorecol), maleic hydrazide, glyphosate, glyphosine, long chain fatty alcohols and acids, dikegulac, fluoridamid, mefluidide, substituted quaternary ammonium an phosphonium compounds (eg. chlormequat* chlorphonium or mepiquatchloride), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, and tecnazene. Synergy will be most likely to occur with those of the foregoing which are quaternary ammonium compounds in particular those marks with an asterick.

The use of the compounds of general formula (I) in conjunction with gibberellins can be useful where it is desired to reduce the plant growth regulating effects of the compounds (eg. where they are to be used as fungicides). Where the compounds are being applied to the soil surrounding the plants or to the roots of the plant, the plant growth regulating effects of the compounds may possibly be reduced by using also certain types of phenoxybenzoic acids and their derivatives.

The following Examples illustrate the invention; the temperatures are given in degrees Centrigrade (°C.).

EXAMPLE 1

This Example illustrates the preparation of 1-phenyl-1-(1,2,4-triazol-1-yl)methylcyclopentane (Compound No. 1 of Table I).

A mixture of sodium hydroxide (8.0 g) and tetrabutylammonium hydrogen sulphate (34.0 g) in water (100 ml) was added over 15 minutes to a briskly stirred mixture of phenylacetonitrile (11.7 g) and 1,4-dibromobutane (43.2 g) in dichloromethane (100 ml). The mixture was heated at 65° C. for 10 hours, then allowed to cool. The aqueous and organic layers were separated and the aqueous layer was extracted with further dichloromethane. The combined organic layers were washed with water, treated with magnesium sulphate and charcoal, concentrated, then flushed through a column of silica gel using ether as eluant (to remove the ammonium salt) and concentrated to give a yellow oil (43.9 g). Most of the excess dibromide was removed by distillation and the residue was chromatographed on a column of silica gel using 20% ether in 40°–60° C. petrol as eluant to give 1-cyano-1-phenylcyclopentane (4.65 g, 27%) as an almost colourless oil.

Concentrated sulphuric acid (17 ml) was added dropwise to a stirred solution of 1-cyano-1-phenylcyclopentane (4.51 g) in dry methanol (70 ml) and the mixture was heated at 120° C. (external temperature) for 24 hours. After cooling, the mixture was poured into water and extracted with ether. The extracts were washed successively with water, aqueous sodium bicarbonate (X 2), and water, then dried over magnesium sulphate and concentrated to give a ca. 3:7 mixture of the starting nitrile: 1-methoxycarbonyl-1-phenylcyclopentane respectively (4.35 g) as an almost colourless oil.

A solution of part of this oil (4.20 g) in dry diethyl ether (30 ml) was added over 20 minutes at room temperature to a stirred suspension of lithium aluminium hydride (2.35 g) in diethyl ether (270 ml) under an atmosphere of nitrogen. After 1.5 hours, aqueous ammonium chloride was carefully added, the organic and aqueous layers were separated, and the latter was extracted with fresh ether. The combined extracts were washed successively with water, dilute hydrochloric acid (X 2), water aqueous sodium bicarbonate (X 2), and water, then dried over magnesium sulphate and concentrated to give 1-hydroxymethyl-1-phenylcyclopentane (2.65 g, 59% from 1-cyano-1-phenylcyclopentane), $^1$H n.m.r. (CDCl$_3$): δ 3.48 (2H, s, C$\underline{H}_2$OH).

A solution of methanesulphonyl chloride (1.62 g) in dry dichloromethane (10 ml) was added over 20 minutes to a stirred mixture of 1-hydroxymethyl-1-phenylcyclopentane (1.91 g) and triethylamine (1.64 g) in dry dichloromethane (50 ml) at 0° C. (white precipitate). After 1 hour, all at about 0° C., water was added to the reaction mixture and the organic and aqueous layers were separated. The organic layer was washed successively with dilute hydrochloric acid, water, aqueous sodium bicarbonate and water, then dried over magnesium sulphate and concentrated to give almost pure 1-methanesulphonyloxymethyl-1-phenylcyclopentane (2.85 g) as an almost colourless oil which crystallised completely on standing in the fridge, melting point 55°–60° C., $^1$H n.m.r. (CDCl$_3$): δ 2.51 (3H, s, C$\underline{H}_3$SO$_2$), 4.16 (2H, s, C$\underline{H}_2$OSO$_2$CH$_3$).

A solution of part of this solid (1.99 g) in dry dimethylformamide (DMF: 10 ml) was added to a stirred solution of sodium triazole [from 1,2,4-triazole (0.65 g) and sodium hydride (0.21 g)] in DMF (30 ml) under an atmosphere of nitrogen. The resulting solution was heated at 160° C. for 2 hours then allowed to cool, diluted with water, and extracted with ether. The extracts were washed with water, dried over magnesium sulphate, then concentrated to give a white solid (1.27 g) which was washed thoroughly with 40°–60° petrol and dried in vacuo to give the title compound (0.94 g, 55% from 1-hydroxymethyl-1-phenylcyclopentane) as colourless needles. An analytical sample, recrystallised from dichloromethane/40°–60° petrol, had melting point 106.5°–107.5° C., $^1$H n.m.r. (CDCl$_3$): δ 4.26 (2H, s, C$\underline{H}_2$N), Found: C, 74.24; H, 7.49; N, 18.77%. C$_{14}$H$_{17}$N$_3$ requires C, 73.97; H, 7.54; N, 18.49%.

EXAMPLE 2

This Example illustrates the preparation of 1-(2,4-dichlorophenyl)-1-(1,2,4-triazol-1-yl)methyl-3-prop-1-ylcylopentane (Compound No. 4 of Table I).

Diethyl prop-1-ylmalonate (70.23 g) was added dropwise to a stirred suspension of sodium hydride (8.35 g) in dimethylformamide (400 ml) under an atmosphere of nitrogen at 10° to 15° C. Following the addition, the mixture was allowed to stir at room temperature until effervescence ceased. The resulting clear solution was cooled again and ethyl bromoacetate (58.06 g) was added. The mixture was heated at 70° C. for 2 hours then allowed to cool, diluted with water, and extracted with ether. The extracts were washed with water, dried over magnesium sulphate, and concentrated to give almost pure diethyl 2-prop-1-yl-2-ethoxycarbonylsuccinate (97.35 g, 97%) as a pale yellow liquid.

A mixture of the part of this liquid (50.30 g), lithium chloride (14.7 g) and water (6.3 ml) in dimethylsulphoxide (465 ml) was heated at 165° C. for 10 hours then allowed to cool. Water was added and the mixture was extracted with ether. The extracts were washed with water, treated with magnesium sulphate and charcoal, and concentrated to give a pale yellow liquid (33.92 g). Distillation gave diethyl 2-prop-1-ylsuccinate (24.62 g, 65%) as a colourless liquid boiling at 126°–131° C. at ca. 10 torr.

A solution of diethyl 2-prop-1-ylsuccinate (23.47 g) in diethyl ether (100 ml) was added dropwise to a cooled and stirred suspension of lithium aluminium hydride (6.19 g) in dry diethyl ether (500 ml) under an atmosphere of nitrogen. When the addition was complete, the reaction mixture was stirred at room temperature for 1.5 hours, then enough water to hydrolyse both the excess reducing agent and the intermediate aluminium complexes was added. The resulting solids were filtered off and the filtrate was dried over magnesium sulphate and concentrated to give 3-hydroxymethylhexan-1-ol (9.58 g, 67%) as a colourless oil.

Methanesulphonyl chloride (16.95 g) was added dropwise to a stirred solution of 3-hydroxymethylhexan-1-ol (8.94 g) in pyridine (39.5 g), maintaining the temperature at less than 5° C. Following the addition, the reaction mixture was stirred at 0° C. for 1.5 hours, then diluted with water and extracted with dichloromethane. The extracts were washed successively with water, dilute hydrochloric acid (X 2), water, aqueous sodium bicarbonate, and water, then dried over magnesium sulphate and concentrated to give 3-methanesulphonyloxymethylhex-1-yl methanesulphonate. (16.13 g, 83%) as a yellow oil.

A suspension of sodium hydride (2.16 g) in dry dimethylsulphoxide (DMSO: 70 ml) was stirred at 50° C. under a nitrogen atmosphere for 2.5 hours and then cooled to 15° C. in an ice bath. A mixture of 2,4-dichlorophenylacetonitrile (8.37 g) and 3-methanesulphonyloxyhex-1-yl methanesulphonate (14.27 g) in DMSO (70 ml) was added dropwise to this solution over 15 minutes. The reaction mixture was stirred at room temperature for 0.5 hours, at 90° C. for 3 hours, and at 130° C. for 2 hours, and was then allowed to cool, diluted with water, and extracted with ether. The extracts were washed with water, dried over magnesium sulphate and concentrated to give a dark coloured oil (7.76 g). Purification of this crude product by bulb-to-bulb distillation gave a mixture of diastereomers of 1-cyano-1-(2,4-dichlorophenyl)-3-prop-1-ylcyclopentane (4.95 g, 39%) as a colourless oil (oven temperature: 230° C., ca. 10 torr).

A mixture of 1-cyano-1-(2,4-dichlorophenyl)-3-prop-1-ylcyclopentane (4.53 g) and sodium hydroxide (4.17 g) in ethylene glycol (45 ml) was heated at 170° C. for 4 hours, then allowed to cool and poured into water. The resulting mixture was washed twice with ether then acidified with concentrated hydrochloric acid and extracted with ether. The ether extracts were washed with water, dried over magnesium sulphate, and concentrated to give a viscous oil (2.82 g). Chromatography on a column of silica gel using 30% ether in 40°–60° C. petrol gave a mixture of diastereomers of 1-carboxy-1-(2,4-dichlorophenyl)-3-prop-1-ylcyclopentane (1.76 g, 36%) as a viscous oil.

A solution of 1-carboxy-1-(2,4-dichlorophenyl)-3-prop-1-ylcyclopentane (1.60 g) in dry tetrahydrofuran (THF: 30 ml) was added to a stirred suspension of lithium aluminium hydride (0.30 g) in THF (20 ml) and the mixture was heated at 60° C. for 60 hours. After cooling, the mixture was poured carefully into a mixture of ice and dilute hydrochloric acid, then extracted with ether. The extracts were washed successively with water, aqueous sodium bicarbonate, and water, then dried over magnesium sulphate and concentrated to give a yellow oil (1.50 g) consisting mainly of a mixture of diastereomers of 1-(2,4-dichlorophenyl)-1-hydroxymethyl-3-prop-1-ylcyclopentane.

This alcohol was converted, via the two stage mesylation then displacement sequence used as described in Example 1 to convert 1-hydroxymethyl-1-phenylcyclopentane into 1-phenyl-1-(1,2,4-triazol-1-yl)methylcyclopentane, into a 1:3 mixture of diastereomers of the title compound, a yellow oil [34% yield from 1-carboxy-1-(2,4-dichlorophenyl)-3-prop-1-ylcyclopentane], $^1$H n.m.r. (CDCl$_3$): 4.49 and 4.72 (each a doublet, J 15 Hz, CH$_2$N of major diastereomer), m/e (chemical ionisation: ammonia) 338 and 340 as strongest and next to strongest peaks respectively (MH+).

EXAMPLE 3

This Example illustrates the preparation of 1-(2,4-dichlorophenyl)-1-(1,2,4-triazol-1-yl)methyl-3-methylcyclopentane (Compound No. 2 of Table I).

Phosphorus tribromide (61.2 g) was added dropwise to paddle-stirred 2-methylbutan-1,4-diol (31.2 g) at between 0° and −10° C. (strong exotherm). When the addition was complete the mixture was stirred at room temperature for 1.5 hours then allowed to stand overnight. Distillation of the reaction mixture gave 1,4-dibromo-2-methylbutane (34.1 g, 49%) as a liquid.

A suspension of sodium hydride (3.68 g) in dry dimethylsulphoxide (DMSO: 75 ml) was stirred at 50° C. under a nitrogen atmosphere for 1.5 hours and then allowed to cool. A mixture of 2,4-dichlorophenylacetonitrile (13.02 g) and 1,4-dibromo-2-methylbutane (17.73 g) in dry diethyl ether (110 ml) was added dropwise with stirring to the resulting clear solution at between 25° and 35° C. It was then stirred at room temperature for 3 hours, allowed to stand overnight, poured into ice and water, and extracted with ether. The extracts were washed with water, dried over magnesium sulphate, and concentrated to give a golden coloured oil (18.83 g). Chromatography on a column of silica gel using 10% ether in 40°-60° C. petrol as eluant gave a mixture of diastereomers of 1-cyano-1-(2,4-dichlorophenyl)-3-methylcyclopentane (9.0 g, 51%) as a yellow oil. Found: C, 61.87; H, 5.03; N, 5.53%. C$_{13}$H$_{13}$Cl$_2$N requires C, 61.42; H, 5.12; N, 5.52%.

A mixture of 1-cyano-1-(2,4-dichlorophenyl)-3-methylcyclopentane (0.50 g) and 48% aqueous hydrogen bromide (5.0 ml) were heated at 140° to 145° C. for 60 hours and then allowed to cool. The mixture was poured into ice and water and extracted with ether. The extracts were washed with water, dried over magnesium sulphate and concentrated to give an oil (0.35 g) which partially crystallised. This crude material was dissolved in dichloromethane and extracted with aqueous sodium bicarbonate. These bicarbonate extracts were washed with dichloromethane, then acidified with concentrated hydrochloric acid and extracted with dichloromethane. These dichloromethane extracts were washed with water, dried over magnesium sulphate, and concentrated to give a mixture of diastereomers of 1-carboxy-1-(2,4-dichlorophenyl)-3-methylcyclopentane (0.25 g, 47%) as a solid, melting point 136°-137° C., IR (nujol mull): 1695 cm$^{-1}$, $^1$H n.m.r. (CDCl$_3$): δ0.97, 1.04, 1.09 (CH$_3$).

1-Carboxy-1-(2,4-dichlorophenyl)-3-methylcyclopentane was converted, via the 3 stage sequence described in Example 2 for the conversion of 1-carboxy-1-(2,4-dichlorophenyl)-3-prop-1-ylcyclopentane into 1-(2,4-dichlorophenyl)-1-(1,2,4-triazol-1-yl)methyl-3-prop-1-ylcyclopentane, into a 1:2 mixture of diastereomers of the title compound, a viscous oil (19% yield over the 3 stages), $^1$H n.m.r. (CDCl$_3$): δ1.09 and 1.15 (main CH$_3$ absorptions), 4.42, 4.55, 4.58, 4.66, 4.81, (CH$_2$N), m/e (chemical ionisation: ammonia) 310 and 312 as strongest and next to strongest peaks respectively (MH+).

EXAMPLE 4

This Example illustrates the preparation of 2-(4-chlorophenyl)-2-(1,2,4-triazol-1-yl)methyl-cyclohexanone. (Compound No 6 of Table I).

Magnesium turnings (6.15 g) and 4-chloro-iodobenzene (59.6 g) were warmed in dry ether (300 ml) until all the magnesium had dissolved. The solution was stirred for 30 minutes. 2-Chlorocyclohexanone (30 g) in dry ether (150 ml) was added dropwise at rate sufficient to maintain gentle reflux. After the addition was complete dry toluene (400 ml) was run in and the ether distilled off. The resulting sodium was heated at reflux for 4 hours, then cooled and poured into a large excess of 30% aqueous ammonium chloride. The organic layer was separated, washed with water then dried over anhydrous magnesium sulphate. The solvent was removed in vacuo and the resulting oil crystallised and recrystallised from ether/hexane after decolourising with charcoal. An off-white solid was obtained (25.1 g), melting point 76°-78° C. This was 2-(4-chlorophenyl)-cyclohexanone.

This solid (10 g) was dissolved in dimethylsulphoxide (80 ml) and a few drops of 0.5N sodium ethoxide were added followed by paraformaldehyde (1.65 g). The solution was heated at 60° C. for 4 hours, allowed to cool, then thrown into water (200 ml). The water was extracted with ether (2×100 ml) and the combined organic layers dried over magnesium sulphate then concentrated in vacuo. The resulting oil was chromatographed on silica using a 1:1 mixture of hexane and dichloromethane as eluant. 2-(4-chlorophenyl)-2-hydroxymethyl-cyclohexanone (5.1 g) was obtained as a colourless oil.

A solution of this oil (2.39 g) in pyridine (20 ml) was cooled to 0° C. and methanesulphonylchloride (2.29 g) was added with stirring. The mixture was allowed to warm to room temperature, stirred for 3 hours, allowed to stand overnight, then poured into water. The water was extracted with ether (2×50 ml). The ether solution was washed with 2N HCl, then with water, dried over magnesium sulphate and concentrated in vacuo. 2-(4-chlorophenyl)-2-methanesulphonyloxymethylcyclohexanone (2.6 g) was obtained as a viscous oil, and used without further purification.

Sodium hydride (0.39 g) free of oil was added to a solution of 1,2,4-triazole (1.12 g) in dry DMF (20 ml) and the mixture stirred for 15 minutes. The methanesulphonyloxy compound (2.48 g) prepared as described above was added in dry DMF (10 ml). After addition the mixture was heated and stirred at 100° C. for 5 hours, allowed to cool, then thrown into water. The water was extracted with ether (2×50 ml) and the ether dried over magnesium sulphate and concentrated in vacuo. The residue was chromatographed on silica with a 1:1 mixture of ethyl acetate and hexane as eluant. The title compound was obtained as a viscous oil. $^1$H n.m.r. (CDCl$_3$): δ4.38(2H, dd, C$\underline{H}_2$N); IR(nujol mull): 1705 cm$^{-1}$ (γC=O).

EXAMPLE 5

This Example illustrates the preparation of 2-(4-chlorophenyl)-2-(1,2,4-triazol-1-yl)methyl-cyclohexanol. (Compound No 7 of Table I).

2-(4-Chlorophenyl)-2-(1,2,4-triazol-1-yl)methylcyclohexanone (400 mg) was dissolved in methanol (10 ml) and sodium borohydride (200 mg) was added. The mixture was stirred at room temperature for 2 hours, then poured into water. The water was extracted with ethyl acetate (2×30 ml). The ethyl acetate was dried over magnesium sulphate then concentrated in vacuo to give the title compound as a viscous oil (360 mg). $^1$H n.m.r. (CDCl$_3$): δ4.41(2H, dd, C$\underline{H}_2$N), 3.86 (1H, m, C$\underline{H}$OH): IR(nujol mull): 3330 cm$^{-1}$ (γO—H).

EXAMPLE 6

This Example illustrates the preparation of 2-(4-chlorophenyl)-2-(1,2,4-triazol-1-yl)methyl-1-methylcyclohexanol. (Compound No 8 of Table 1).

Magnesium turnings (0.25 g) were added to methyl iodide (1.42 g) in dry ether (20 ml) and the mixture refluxed until all the magnesium had dissolved. 2-(4-Chlorophenyl)-2-(1,2,4-triazol-1-yl)methyl-cyclohexanone (0.99 g) in dry ether (10 ml) was added. The mixture was then refluxed for 3 hours, cooled and poured into excess 30% aqueous ammonium chloride. The mixture was then extracted with ethyl acetate (2×30 ml) and the ethyl acetate dried over magnesium sulphate and concentrated in vacuo. The residue was recrystallised from hexane containing a little ether to give the title compound as a white solid (400 mg). Melting point: 172.5°–175.0° C. $^1$H n.m.r. (CDCl$_3$): δ4.71(2H, dd, C$\underline{H}_2$N), 1.36 (3H, s, C$\underline{H}_3$); IR(nujol mull); 3330 cm$^{-1}$ (γO—H).

EXAMPLE 7

An emulsifiable concentrate was made up by mixing the ingredients, and stirring the mixture until all the constituents were dissolved.

| Compound of Example 1 | 10% |
| --- | --- |
| Ethylene dichloride | 40% |
| Calcium dodecylbenzenesulphate | 5% |
| "Lubrol" L | 10% |
| "Aromasol" H | 35% |

EXAMPLE 8

A composition in the form of grains readily dispersible in a liquid, eg. water, was prepared by grinding together the first three ingredients in the presence of added water and then mixing in the sodium acetate. The resultant mixture was dried and passed through a British Standard mesh sieve, size 44–100, to obtain the desired size of grains.

| Compound of Example 2 | 50% |
| --- | --- |
| "Dispersol" T | 25% |
| "Lubrol" APN5 | 1.5% |
| Sodium acetate | 23.5% |

EXAMPLE 9

The ingredients were all ground together to produce a powder formulation readily dispersible in liquids.

| Compound of Example 3 | 45% |
| --- | --- |
| "Dispersol" T | 5% |
| "Lissapol" NX | 0.5% |
| "Cellofas" B600 | 2% |
| Sodium acetate | 47.5% |

EXAMPLE 10

The active ingredient was dissolved in a solvent and the resultant liquid was sprayed on to the granules of China clay. The solvent was then allowed to evaporate to produce a granular composition.

| Compound of Example 1 | 5% |
| --- | --- |
| China clay granules | 95% |

EXAMPLE 11

A composition suitable for use as a seed dressing was prepared by mixing the three ingredients.

| Compound of Example 1 | 50% |
| --- | --- |
| Mineral oil | 2% |
| China clay | 48% |

EXAMPLE 12

A dusting powder was prepared by mixing the active ingredient with talc.

| Compound of Example 1 | 5% |
| --- | --- |
| Talc | 95% |

EXAMPLE 13

A Col formulation was prepared by ball-milling the constituents set out below and then forming an aqueous suspension of the ground mixture with water.

| Compound of Example 1 | 40% |
| --- | --- |
| "Dispersol" T | 10% |
| "Lubrol" APN5 | 1% |
| Water | |

EXAMPLE 14

A dispersible powder formulation was made by mixing together the ingredients set out below and then grinding the mixture until all were thoroughly mixed.

| Compound of Example 4 | 25% |
| --- | --- |
| "Aerosol" OT/B | 2% |
| "Dispersol" A.C. | 5% |
| China clay | 28% |
| Silica | 40% |

EXAMPLE 15

This Example illustrates the preparation of a dispersible powder formulation. The ingredients were mixed and the mixture then ground in a comminution mill.

| Compound of Example 1 | 25% |
|---|---|
| "Perminal" BX | 1% |
| "Dispersol" T | 5% |
| Polyvinylpyrrolidone | 10% |
| Silica | 25% |
| China clay | 34% |

EXAMPLE 16

The ingredients set out below were formulated into a dispersible powder by mixing then grinding the ingredients.

| Compound of Example 2 | 25% |
|---|---|
| "Aerosol" OT/B | 2% |
| "Dispersol" A | 5% |
| China clay | 68% |

In Examples 7 to 16 the proportions of the ingredients given are by weight. The remaining compounds of Table I were all similarly formulated as per Examples 7 to 16.

There now follows an explanation of the compositions or substances represented by the various Trade Marks and Trade Names mentioned above.

LUBROL L: a condensate of nonyl phenol (1 mole) with ethylene oxide (13 moles)

AROMASOL H: a solvent mixture of alkylbenzenes

DISPERSOL T AND AC: a mixture of sodium sulphate and a condensate of formaldehyde with sodium naphthalene sulphonate LUBROL APN5: a condensate of nonyl phenol (1 mole) with naphthalene oxide (5.5 moles)

CELLOFAS B600: a sodium carboxymethyl cellulose thickener

LISSAPOL NX: a condensate of nonyl phenol (1 mole) with ethylene oxide (8 moles)

AEROSOL OT/B: dioctyl sodium sulphosuccinate

PERMINAL BX: a sodium alkyl naphthalene sulphonate

EXAMPLE 17

The compounds were tested against a variety of mainly foliar fungal diseases of plants. The techniques employed were as follows.

For all tests other than that against *Botrytis cinerea*, the plants were grown in John Innes Potting Compost (No. 1 or 2) in 4 cm diameter minipots. A layer of fine sand was placed at the bottom of the pots containing the dicotyledonous plants to facilitate uptake of test compounds by the roots. The test compounds were formulated either by bead milling with aqueous Dispersol T or as a solution in acetone or acetone/ethanol which was diluted to the required concentration immediately before use. For the foliage diseases, solutions and suspensions (100 ppm ai.) were sprayed on the foliage and applied to the roots of the plant via the soil. For the test against *Botrytis cinerea*, grape berries were sprayed with the test compounds. The sprays were applied to maximum retention and the root drenches to a final concentration equivalent to approximately 40 ppm ai./dry soil. Tween 20, to give a final concentration of 0.05%, was added when the sprays were applied to cereals. (ai. means "active ingredient").

Most were protectant tests when the compound was applied to the soil and roots and to the foliage one or two days before the plant was inoculated with the pathogen. However, in the case of the tests against *Erysiphe graminis hordei* and *Botrytis cinerea*, the treatment was eradicative and the compounds were applied one day after inoculation.

Inoculation of the grape berries in the *Botrytis cinerea* test was achieved by slitting fruits twice and then immersing them in a spore suspension of the pathogen. The remaining foliar pathogens were applied by spraying as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:

4 = no disease
3 = trace to 5% of disease on untreated plants
2 = 6–25% of disease on untreated plants
1 = 26–59% of disease on untreated plants
0 = 60–100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | BOTRYTIS CINEREA (GRAPE) | CERCOSPORA ARACHIDICOLA (PEANUT) | VENTURIA INAEQUALIS (APPLE) |
|---|---|---|---|---|---|---|
| 1 | 4 | 4 | — | 0 | 3 | 4 |
| 2 | 3 | 4 | 1 | — | — | 4 |
| 3 | 3 | 4 | 2 | — | 4 | 4 |
| 4 | 4 | 4 | 3 | — | 4 | 4 |
| 5 | 4 | 4 | 2 | — | 4 | 0 |

— = no data available

EXAMPLE 18

This Example illustrates the plant growth regulating properties of the compounds. The compounds were applied as an overall spray of an emulsifiable concentrate diluted to give the concentrations shown in Table III. The plants were grown in 3" pots in peat compost and sprayed at the 2 leaf stage. Plant growth regulating effects were assessed 13 or 19 days after application of the compounds. Retardation of growth was scored on a 1-3 scale where:

1 = 0–30% retardation
2 = 31–75% retardation
3 = 75% retardation or more.

The absence of any numeral 1 to 3 signifies no effect.

Additional plant growth regulating properties are indicated as follows:

G=darker green leaf colour
A=apical effect
T=tillering effect

The results are shown in Table III. If no figure is shown the compound was substantially inactive as a stunting agent.

TABLE III

| COMPOUND | DAT | RATE (ppm) | AT | CC | DA | LT | SB | TO | SY | CT | MZ | WW | BR | VN |
|---|---|---|---|---|---|---|---|---|---|---|---|---|---|---|
| 1 | 18 | 4000 | — | — | — | 1 | 1 | 2GT | 1GAT | 3AT | 1 | — | — | — |
| 2 | 18 | 4000 | — | — | — | 3HA | 3GA | 3A | 3GA | 3GA | 2A | — | — | — |
| 3 | 18 | 4000 | — | — | — | 3GA | 3GA | 3GA | 3GA | 3A | 2 | 1 | 1 | 3GA |
| 4 | 18 | 4000 | — | — | — | 3A | 3GA | 3GA | 3GA | 3A | 2 | — | 1 | 3GA |
| 5 | 18 | 4000 | 1 | 1 | 1 | 3G | 3G | 3G | 2G | 3GA | — | — | — | 3GA |
| 6 | 18 | 4000 | — | — | — | A | 3GA | 1G | 2GAT | — | — | 1 | 1 | 3GA |
| 7 | 18 | 4000 | 3G | 3G | 1G | — | 2G | 2G | 1GAT | — | 3 | 1 | 1 | 2 |
| 8 | 18 | 4000 | G | G | G | 1 | — | — | — | — | — | — | — | — |

Key to test species in Table III
AT *Agrostis tenuis*
CC *Cynosurus cristatus*
DA *Dactylis glomerata*
LT *Lactuca sativa*
SB *Beta vulgaris*
TO *Lycopersicum esculentum*
SY *Glycine max*
CT *Gossypium hirsutum*
MZ *Zea mays*
WW *Triticum aestivum*
BR *Hordeum vulgare*
VN *Vitus vinifera*

We claim:

1. A compound having the general formula (I):

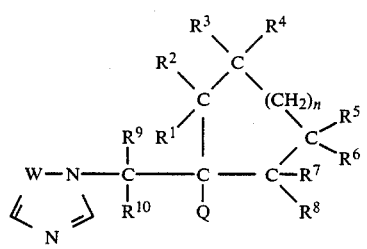

and stereoisomers thereof, wherein W is N; Q is phenyl or halophenyl; $R^1$, $R^2$, $R^3$ and $R^4$, which may be the same or different, are H, hydroxy, or alkyl containing from 1 to 6 carbon atoms; $R^5$, $R^6$, $R^7$, $R^8$, $R^9$ and $R^{10}$ are hydrogen; n is 0 or 1; and acid salts and metal complexes thereof.

2. A compound according to claim 1 wherein W is N; Q is $C_6H_5$; $R^1$, $R^2$, $R^3$ and $R^4$ are hydrogen; and n is 0.

3. A compound according to claim 1 wherein W is N; Q is 2,4—di—Cl—$C_6H_3$; $R^1$, $R^2$ and $R^4$ are hydrogen; $R^3$ is $CH_3$ and n is 0.

4. A compound according to claim 1 wherein W is N; Q is 4—Cl—$C_6H_4$; $R^1$, $R^2$ and $R^4$ are hydrogen; $R^3$ is $CH_3$ and n is 0.

5. A compound according to claim 1 wherein W is N; Q is 2,4—di—Cl—$C_6H_3$; $R^1$, $R^2$ and $R^4$ are hydrogen; $R^3$ is n—$C_3H_7$ and n is 0.

6. A compound according to claim 1 wherein W is N; Q is 4—Cl—$C_6H_4$; $R^1$ and $R^2$ are hydrogen; $R^3$ and $R^4$ are $CH_3$ and n is 0.

7. A compound according to claim 1 wherein W is N; Q is 4—Cl—$C_6H_4$; $R^1$ and $R^2$ are hydrogen; $R^3$ and $R^4$ are H and n is 1.

8. A compound according to claim 1 wherein W is N; Q is 4—Cl—$C_6H_4$; $R^1$ is OH; $R^2$, $R^3$ and $R^4$ are hydrogen; and n is 1.

9. A compound according to claim 1 wherein W is N; Q is 4—Cl—$C_6H_4$; $R^1$ is OH; $R^2$ is $CH_3$; $R^3$ and $R^4$ are hydrogen and n is 1.

10. A fungicidal or plant growth regulating composition comprising an effective amount of a compound of general formula (I) as defined in claim 1; and a carrier or diluent therefor.

11. A method of combatting fungi, which comprises applying to a plant, to seed of a plant, or to the locus of the plant or seed, an effective amount of a compound as defined in claim 1.

12. A method of regulating plant growth, which comprises applying to the plant, to seed of a plant or to the locus of a plant or seed, an effective amount of a compound as defined in claim 1.

* * * * *